United States Patent [19]

Napier et al.

[11] Patent Number: 4,678,791

[45] Date of Patent: Jul. 7, 1987

[54] 6-PHENYL-1,2-3,4,4A,5-6,10B-OCTAHYDROBENZ(H)ISOQUINOLINES USEFUL FOR TREATING DEPRESSION

[75] Inventors: James J. Napier, Chili; Ronald C. Griffith, Pittsford, both of N.Y.

[73] Assignee: Pennwalt Corporation, Philadelphia, Pa.

[21] Appl. No.: 731,426

[22] Filed: May 7, 1985

[51] Int. Cl.$^4$ .................... A61K 31/47; C07D 221/10
[52] U.S. Cl. .................................. 514/290; 546/101; 558/341; 558/426
[58] Field of Search .......................... 546/101; 514/290

[56] References Cited

U.S. PATENT DOCUMENTS 4,022,792  5/1977  Albertson et al. ............... 546/101 X
4,150,136  4/1979  Bastian ................................ 514/290
4,517,187  5/1985  Griffith .............................. 514/250

FOREIGN PATENT DOCUMENTS

19555/83  5/1984  Australia .
83/6448  7/1984  South Africa .

OTHER PUBLICATIONS

Borch, et al., J. Am. Chem. Soc., vol. 93, No. 12, pp. 2897–2904 (1971).

Primary Examiner—Donald G. Daus
Assistant Examiner—Diana G. Rivers

[57] ABSTRACT

6-Phenyl-1,2,3,4,4a,5,6,10b-octahydrobenz(h)isoquinolines having anti-depressant activity and methods for their preparation.

7 Claims, No Drawings

6-PHENYL-1,2-3,4,4A,5-6,10B-OCTAHYDROBENZ(-H)ISOQUINOLINES USEFUL FOR TREATING DEPRESSION

BACKGROUND OF THE INVENTION

This invention pertains to a series of novel 6-phenyl-1,2,3,4,4a,5,6,10b-octahydrobenz(h)isoquinolines with anti-depressant activity.

The synthesis of the cis and trans isomers of the parent 1,2,3,4,4a,5,6,10b-octahydrobenz(h)isoquinoline ring system has been reported (W. Oppolozer, *Tetrahedron Letters*, 1974, 1001), however no biological data was presented.

A series of 8,9-dihydroxy-1,2,3,4,4a,5,6,10b-octahydrobenz(h)isoquinolines has been prepared and reported to lower blood pressure and heart rate in anesthetized cats. (J. G. Cannon, et al, *Journal of Medicinal Chemistry*, 1980, 23, 502).

BRIEF SUMMARY OF THE INVENTION

The compounds of the invention are those of the formula (I):

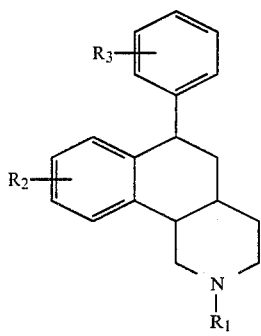

I wherein
- $R_1$ is hydrogen, $C_1$–$C_7$ alkyl, or $C_4$–$C_8$ cycloalkylmethyl;
- $R_2$ is hydrogen or a single or multiple substitution of hydroxyl, halogen, $C_1$–$C_7$ alkoxy, or $C_1$–$C_7$ alkyl; and
- $R_3$ is hydrogen or a single or multiple substitution of hydroxyl, halogen, $C_1$–$C_7$ alkoxy, phenoxy, $C_1$–$C_7$ alkyl, or trifluoromethyl; all stereoisomeric forms and mixtures thereof, and pharmaceutically acceptable acid addition salts thereof. The compounds are useful in the field of mental health as anti-depressants.

The invention also includes pharmaceutical preparations containing one or more of the above compounds as an active ingredient and methods for administering the pharmaceutical preparations to a human or other mammal in need of anti-depressant treatment. In addition, it includes processes for making the compounds.

DETAILED DESCRIPTION

Compounds

The compounds of the invention are those of the formula (I):

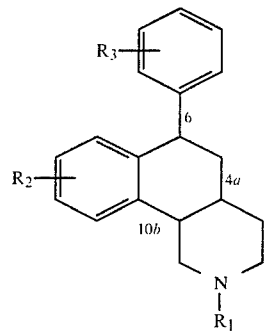

I wherein
- $R_1$ is hydrogen, $C_1$–$C_7$ alkyl, or $C_4$–$C_8$ cycloalkylmethyl;
- $R_2$ is hydrogen or a single or multiple substitution of hydroxyl, halogen, $C_1$–$C_7$ alkoxy, or $C_1$–$C_7$ alkyl; and
- $R_3$ is hydrogen or a single or multiple substitution of hydroxyl, halogen, $C_1$–$C_7$ alkoxy, phenoxy, $C_1$–$C_7$ alkyl, or trifluoromethyl; all stereoisomeric forms and mixtures thereof and pharmaceutically acceptable acid addition salts thereof.

Positions 4a, 6 and 10b are designated accordingly.

The notation, "$C_1$–$C_7$ alkyl", refers to an alkyl group of one to seven carbon atoms, straight or branched. The notation, "$C_1$–$C_7$ alkoxy" refers to an alkoxy group of one to seven carbon atoms, straight or branched. The notation, "$C_4$–$C_8$ cycloalkylmethyl" refers to a cycloalkyl group of three to seven carbon atoms, joined to a methylene group, the methylene group providing the point of attachment of the remainder of the compound. "Halogen" means chlorine bromine, fluorine or iodine. Multiple substitution of an $R_2$ moiety means two to four substitutions of that moiety. Multiple substitution of an $R_3$ moiety means two to five substitutents of that moiety. Each $R_2$ or $R_3$ substituent in an embodiment of the compound of formula I can be selected independently of the nature of any other $R_2$ or $R_3$ substitutent in that embodiment. In the preferred compounds, $R_2$ and $R_3$ are independently either a single or double substitution.

The compounds of formula I have asymmetric centers at positions 4a, 6, and 10b. Therefore, they may occur in any one of the following stereoisomeric forms: as anyone of four diastereoisomeric forms and as either of the two optically active enantiomeric forms that comprise each diastereoisomeric form. The invention includes all of the stereoisomeric forms as well as mixtures thereof.

SYNTHESIS OF COMPOUNDS

In the preferred process for preparing the compounds of this invention, a 4-phenyl-3,4-dihydronaphthalen-1(2H)-one of formula II

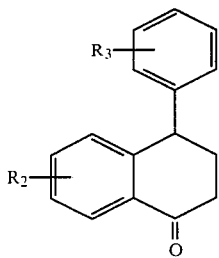

where $R_2$ and $R_3$ are defined above are reacted sequentially with:
(1) trimethylsilyl cyanide and zinc iodide in dichloromethane solution,
(2) aqueous hydrochloric acid in methanol and tetrahydrofuran (THF) solution,
(3) thionyl chloride and pyridine,
(4) followed by heating to approximately 100° C. in pyridine to produce the corresponding 1-cyano-4-phenyl-3,4-dihydronaphthalene of formula III

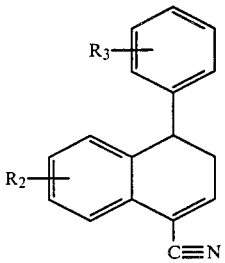

4-Phenyl-3,4-dihydronaphthalene-1(2H)-ones of formula II with any of the combinations of $R_2$ and $R_3$ groups defined above [i.e. $R_2$ is a single or multiple substitution of hydrogen, hydroxyl, halogen, $C_1$–$C_7$ alkoxy or $C_1$–$C_7$ alkyl; $R_3$ is a single or multiple substitution of hydrogen, hydroxyl, halogen, $C_1$–$C_7$ alkoxy, phenoxy, $C_1$–$C_7$ alkyl or trifluoromethyl] can be synthesized. Examples of 4-phenyl-3,4-dihydronaphthalene-1(2H)-ones are:

4-phenyl-3,4-dihydronaphthalen-1(2H)-one, [See *Journal of the American Chemical Society*, 1954, 76; 1641];
4-(4-bromophenyl)-3,4-dihydronaphthalen-1(2H)-one,
4-[4-(trifluoromethyl)phenyl)]-3,4-dihydronaphthalen-1(2H)-one,
4-(2,4-dichlorophenyl)-3,4-dihydronaphthalen-1(2H)-one,
4-(3,4-dichlorophenyl)-3,4-dihydronaphthalen-1(2H)-one,
4-(4-fluorophenyl)-3,4-dihydronaphthalen-1(2H)-one,
4-[3-(trifluoromethyl)phenyl]-3,4-dihydronaphthalen-1(2H)-one,
4-(3-methoxy-4-fluorophenyl)-3,4-dihydronaphthalen-1(2H)-one
4-(4-methoxyphenyl)-3,4-dihydronaphthalen-1(2H)-one,
4-(3-methoxyphenyl)-3,4-dihydronaphthalen-1(2H)-one,
4-(2-methoxyphenyl)-3,4-dihydronaphthalen-1(2H)-one,
4-(4-n-butoxyphenyl)-3,4-dihydronaphthalen-1(2H)-one,
4-(4-phenoxyphenyl)-3,4-dihydronaphthalen-1(2H)-one, [See the *Journal of Medicinal Chemistry*, 1984, 27, 1508];
8-chloro-5-methoxy-4-phenyl-3,4-dihydrophthalen-1(2H)-one,
5-methoxy-4-phenyl-3,4-dihydrophthalen-1(2H)-one, [See the *Journal of Organic Chemistry*, 1975, 40, 1216];
4-(2-fluorophenyl)-3,4-dihydrophthalen-1(2H)-one,
4-(3-fluorophenyl)-3,4-dihydrophthalen-1(2H)-one,
4-(2-chlorophenyl)-3,4-dihydrophthalen-1(2H)-one,
4-(3-chlorophenyl)-3,4-dihydrophthalen-1(2H)-one,
4-(3-methylphenyl)-3,4-dihydrophthalen-1(2H)-one,
4-(4-methylphenyl)-3,4-dihydrophthalen-1(2H)-one, [See *ZH. Org. Khim.*, 1982, 18, 870];
5-methoxy-4-(2-methoxyphenyl)-3,4-dihydronaphthalen-1(2H)-one,
7-methoxy-4-(2-methoxyphenyl)-3,4-dihydronaphthalen-1(2H)-one,
7-methoxy-4-phenyl-3,4-dihydrophthalen-1(2H)-one,
7-methoxy-4-(4-methoxyphenyl)-3,4-dihydrophthalen-1(2H)-one, [See *Tetrahedron Letters*, 1980, 21, 1887]; 7-methyl-4-phenyl-3,4-dihydrophthalen-1(2H)-one, 7-methyl-4-(2,4,6-trimethylphenyl)-3,4-dihydrophthalen-1(2H)-one, [See *Collect. Czech. Chem. Commun.*, 1972, 37, 1195]; 7-fluoro-4-(4-fluorophenyl)-3,4-dihydrophthalen-1(2H)-one, [See *Collect. Czech. Chem. Commun.*, 1978, 43, 1760];
6,7-dimethoxy-4-(3,4-dimethoxyphenyl)-3,4-dihydrophthalen-1(2H)-one, [See the *Journal of the Chemical Society Perkin Transactions* 1, 1981, 2920]; 6-methyl-4-(4-methylphenyl)-3,4-dihydrophthalen-1(2H)-one, [See *Tetrahedron Letters*, 1981, 22, 2889]; 4-(2,3,4,5-tetrafluorophenyl)-3,4-dihydrophthalen-1(2H)-one, [See the *Journal of the Chemical Society Perkin Transactions* 1, 1974, 2698]; 7-methoxy-4-[3-(trifluoromethyl)phenyl]-3,4-dihydrophthalen-1-(2H)-one, [See Ger. Offen. No. 2,632,862], and 7-chloro-4-(4-chlorophenyl)-3,4-dihydrophthalen-1(2H)-one, [See U.S. Pat. No. 3,769,275].

An unsaturated nitrile of formula III can be converted to the corresponding [i.e., $R_2$ and $R_3$ remain unchanged] 1-cyano-4-phenyl-1,2,3,4-tetrahydro-2-naphthaleneacetic acid methyl ester of formula IV

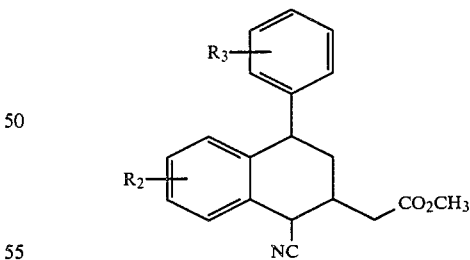

by the four-step sequence of:
(1) the Michael Addition of the sodium salt of dimethylmalonate to the compound of formula III in methanol and tetrahydrofuran solution.
(2) ester hydrolysis of the resulting diester with aqueous potassium hydroxide,
(3) decarboxylation of the diacid produced on hydrolysis by heating in dimethylformamide (DMF) solution, and
(4) esterification with methanol and sulfuric acid.

Catalytic hydrogenation of a compound of formula IV with a platinum oxide catalyst in a solution of acetic acid, tetrahydrofuran and methanol provides the corresponding lactam of formula V

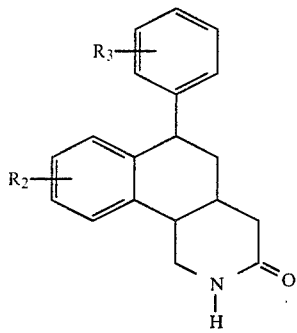

Reduction of a compound of formula V with lithium aluminum hydride in tetrahydrofuran solution or by borane-tetrahydrofuran complex in tetrahydrofuran solution provides the corresponding secondary amine of the compound of formula I where $R_1$ is H.

A compound of formula I where $R_1$ is H can be converted to a corresponding compound of formula I where $R_1$ is $C_2$–$C_7$ alkyl preferably by acylation on the nitrogen atom with the corresponding acyl halide followed by reduction of the resulting amide with borane in tetrahydrofuran. According to this sequence, compounds of formula I where $R_1$ is ethyl, propyl, butyl, pentyl, hexyl, heptyl, or $C_4$–$C_8$ cycloalkylmethyl, may be prepared.

A compound of formula I where $R_1$ is H can be converted to the corresponding compound of formula I where R is methyl preferably by reductive methylation with formaldehyde and formic acid.

As an additional alternative, alkylation on nitrogen of compounds of formula I where $R_1$ is H can be achieved by the general procedure of Borch et al (*Journal of the American Chemical Society*, 1971, 93, 2897) to produce a corresponding compound of formula I where $R_1$ is $C_1$–$C_7$ alkyl. In this procedure, the secondary amine is reacted with an aldehyde and sodium or lithium cyanoborohydride in a solution of methanol and aqueous hydrochloric acid. According to this procedure, the compounds of formula I where $R_1$ is either methyl, ethyl, propyl, butyl, pentyl, hexyl, heptyl, or $C_4$–$C_8$ cycloalkylmethyl may be prepared.

Compounds of formula I where $R_2$ is methoxy and $R_3$ is OH (or $R_2$ is OH and $R_3$ is methoxy) may be prepared using the above methods starting with the corresponding compounds of formula II where $R_2$ is methoxy and $R_3$ is a protected OH (or $R_2$ is a protected OH and $R_3$ is methoxy). A suitable protecting group (e.g. benzyl) may be removed in preference to the methoxy by known methods (e.g. hydrogenolysis).

For compounds of formula I, where $R_2$ and/or $R_3$ is OH, the preferred procedure is to prepare them from the corresponding compound of formula I, where $R_2$ and/or $R_3$ is methoxy, by treatment with aqueous HBr (preferably 48% HBr).

Preparation of the Diastereoisomeric and Enantiomeric Forms of the Compounds of Formula I A compound of formula IV, is synthesized as described above, will exist as a mixture of its four diastereoisomeric forms. If one of those diastereoisomeric forms are purified substantially free of the other three, and is then further processed as described above, the corresponding diastereoisomeric form of the corresponding compound of formula I will be produced substantially free of the other diastereoisomeric forms of that compound of formula I. This can be illustrated for the case where $R_2$ and $R_3$ are both hydrogen as follows:

A mixture of diastereoisomers of the compound of formula IV where $R_2$ and $R_3$ are both hydrogen is separated by chromatography and fractional crystallization to give the four diastereoisimers IVa, IVb, IVc, and IVd (each as an enantiomeric pair).

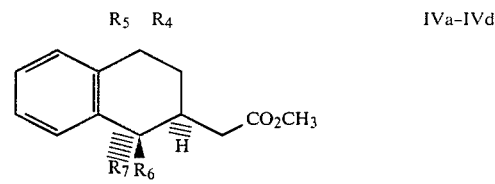

In compound IVa, $R_4$ is phenyl, $R_5$ is hydrogen, $R_6$ is hydrogen and $R_7$ is CN. In compound IVb, $R_4$ is phenyl, $R_5$ is hydrogen, $R_6$ is CN and $R_7$ is hydrogen. In compound IVc, $R_4$ is hydrogen, $R_5$ is phenyl, $R_6$ is CN, and $R_7$ is hydrogen. In compound IVd, $R_4$ is hydrogen, $R_5$ is phenyl, $R_6$ is hydrogen, and $R_7$ is CN.

Compound IVa can be processed according to Scheme 1:

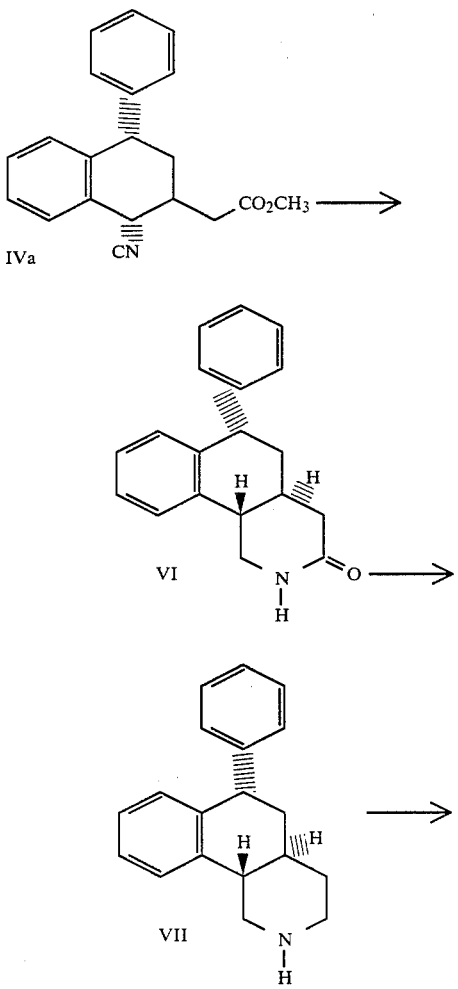

-continued
Scheme 1

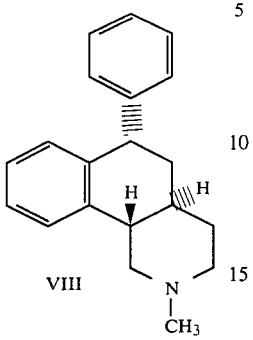

VIII

In Scheme 1, catalytic hydrogenation of the compound of formula IVa over platinum oxide in a solution of tetrahydrofuran, methanol and acetic acid gives the lactam of formula VI. Reduction of the lactam with lithium aluminum hydride in refluxing tetrahydrofuran gives the diastereoisomer of formula VII which is one of the diastereoisomers of the formula I where $R_1$, $R_2$ and $R_3$ are each hydrogen. Reaction of the diastereoisomer of formula VII with 37% aqueous formaldehyde and 88% formic acid provides the diastereoisomer of formula VIII, which is one of the diastereoisomers of formula I where $R_1$ is methyl and $R_2$ and $R_3$ are both hydrogen.

Compound IVc can be processed according to Scheme 2:

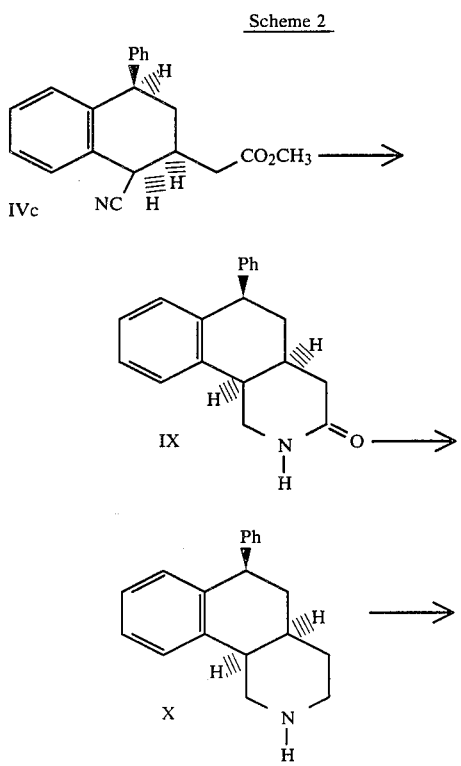

-continued
Scheme 2

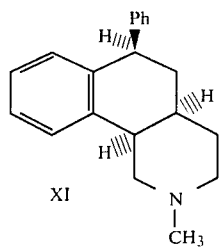

XI

In Scheme 2, a compound of formula IVc is hydrogenated with platinum oxide catalyst in methanol, tetrahydrofuran and acetic acid solution provide the lactam of formula IX. Reduction of the lactam with excess borane-tetrahydrofuran complex gives the diastereoisimer of formula X, which is one of the diastereoisomers of formula I where $R_1$, $R_2$ and $R_3$ are each hydrogen. Reductive methylation of the diastereoisomeric of formula X with 37% aqueous formaldehyde and 88% formic acid provides the diastereoisomer of formula XI, which is one of the diastereoisomers of formula I where $R_1$ is methyl and $R_2$ and $R_3$ are both hydrogen. Scheme 2 can, in analogous fashion, be used to process the compounds IVb and IVd.

Each purified diastereoisomeric form can be further purified by conventional methods for separating a racemic mixture into its components, so that each of its two enantiomeric forms is substantially free of the other. An example of such a method is the reaction of the racemic mixture with a stoichiometric amount of an optically active acid, such as (+)- or (−)-tartaric acid, (+)- or (−)-dibenzoyl tartaric acid, (+)- or (−)-monomethyl tartrate, or other derivative of tartaric acid. The reaction is carried out in a solvent in which the resulting salt of one of the enantiomers of the formula I compound has a different solubility than the resulting salt of the other enantiomer. Methanol, ethanol, or mixtures thereof, are preferred solvents. The preferentially insoluble enantiomer salt is then recovered and converted to the free base of conventional means. If the preferentially insoluble enantiomer salt is still contaminated by an undesirably large amount of the other enantiomer salt, the reaction with tartaric acid or its derivative and the subsequent recovery and conversion steps may be repeated.

Pharmaceutically Acceptable Acid Addition Salts

The pharmaceutically acceptable acid addition salts of the 6-phenyl-1,2,3,4,4a,5,6,10b-octahydrobenz(-h)isoquinoline bases of this invention are prepared by treating those bases with various mineral and organic acids which form non-toxic addition salts having pharmaceutically acceptable anions, such as the hydrochloride, hydrobromide, hydroiodide, sulfate or bisulfate, phosphate or acid phosphate, acetate, lactate, maleate, fumarate, citrate or acid citrate, tartrate or bitartrate, succinate, gluconate, saccharate, methanesulfonate, ethanesulfonate, benzenesulfonate and p-toluenesulfonate salts. For instance, the salt formation step may be carried out by using essentially equimolar amount of the appropriate acid in an aqueous solvent medium or in a suitable organic solvent such as methanol or ethanol.

Anti-depressant Activity

A particularly useful compound with respect to antidepresant activity is the title compound to Example 4, (±)-(4aα,6β,10bα)-2-methyl-6-phenyl- 1,2,3,4,4a,5,6,10b-octahydrobenz(h)isoquinoline (Z)-2-butenedioate (1:1) salt. That compound was tested for antidepressant activity by measuring its ability to inhibit tetrabenazine-induced ptosis in mice.

Male CF-1mice weighing 19-32 grams were housed for a minimum of 5 days under a 12 hour light/dark (6 am/6 pm) schedule at 70°-74° F. and relative humidity of 30-50%. Food and water were available ad libitum until the time of administration of test compounds. Mice in groups of ten were orally administered (via gastric intubation) either the control solution (distilled water 10 ml/kg) or the test compound. The test compound was either dissolved in distilled water or suspended in distilled water containing a drop of polyoxyethylene 20 sorbitan monooleate, sold under the trademark Tween 80. After fifteen minutes, a dose of 10 ml/kg of a solution of tetrabenazine (as its methane sulfonate salt) in distilled water (4 mg/ml) was administered by intravenous injection. The degree of palpebral closure (ptosis) was determined at 30, 60, 90, 120, 150 minutes after administration of the tetrabenazine solution. Each mouse was held by the tail with the front paws supported by a thin wood applicator stick (or pencil) for approximately 10 seconds for each determination. The ptosis was rated on scale of 0 to 4 with each number representing a degree of eye closure:

0 = Eyes fully open—no ptosis
1 = Eyelids closed one-quarter
2 = Eyelids closed one-half
3 = Eyelids closed three-quarters
4 = Eyelids fully closed The lowest active dose (LAD) of the title compound of Example 4, in this assay for antidepressant activity, was 1.25 mg/kg.

INTERMEDIATES AND EXAMPLES

The following specific non-limiting illustrations of synthesis of intermediates and examples of compounds of the invention are provided.

Intermediates

Preparation of 1-Cyano-4-phenyl-3,4-dihydro-naphthalene

To a solution of 4-phenyl-3,4-dihydronaphthalen-1(2H)-one (140.2 g, 0.63 m) in dichloromethane (0.75 L) was added trimethylsilyl cyanide (75.0 g, 0.76 m) and zinc iodide (4.7 g, 0.014 m). The solution was stirred at ambient temperature (about 25° C.) under nitrogen for 17.5 hours. TLC analysis showed the reaction to be complete. The reaction was poured into 0.5N Na$_2$CO$_3$ (500 ml) and dichloromethane (300 ml). The phases were separated and the aqeous phase was extracted with dichloromethane (1×300 ml). The combined dichloromethane extracts were washed successively with 0.5N Na$_2$CO$_3$ (100 ml), 1N HCl (100 ml) and saturated NaCl (100 ml). The dichloromethane extracts were dried over magnesium sulfate and concentrated under vacuum to give 1-cyano-1-trimethylsilyloxy-4-phenyl-1,2,3,4-tetrahydronaphthalene (201 g, 99%) as a thick reddish oil.

The above oil was dissolved in THF (300 ml), methanol (200 ml) and 2N HCl (300 ml) and stirred at ambient temperature under nitrogen for 2 hours. The reaction was poured into water (2 L) and extracted with ethyl acetate (3×500 ml). The combined ethyl acetate extracts were washed successively with water (2×200 ml) and saturated NaCl (200 ml). The ethyl acetate extracts were dried over magnesium sulfate and concentrated under vacuum to give 1-cyano-1-hydroxy-4-phenyl-1,2,3,4-tetrahydronaphthalene (154 g, 98%) as a yellow orange oil.

The above oil was dissolved in dichloromethane (700 ml) and cooled to 0° C. under nitrogen. Pyridine (117 ml, 1.45 m) was added, followed by the dropwise addition of a solution of thionyl chloride (60 ml, 98 g, 0.82 m) in dichloromethane (100 ml). The solution was allowed to warm to ambient temperature and stirred at that temperature overnight. Water (50 ml) was slowly added and the reaction mixture was poured into water (300 ml) and dichloromethane (300 ml). The phases were separated and the aqeous phase was extracted with dichloromethane (300 ml). The combined dichloromethane extracts were washed successively with 2N HCl (2×500 ml) and saturated NaCl (300 ml). The dichloromethane extract was dried over magnesium sulfate and concentrated under vacuum to give 1-chloro-1-cyano-4-phenyl-1,2,3,4-tetrahydronaphthalene (161 g, 95%) as an oil.

The above oil was dissolved in pyridine (300 ml) and heated to 105° C. under nitrogen overnight. The solution was cooled to ambient temperature and dissolved in 3N HCl (700 ml) and ethyl acetate (500 ml). The phases were separated and the aqueous phase was extracted with ethyl acetate (2×500 ml). The combined ethyl acetate extracts were washed successively with 2N HCl (2×200 ml) and saturated NaCl (200 ml). The ethyl acetate extract was dried over magnesium sulfate and the solvent removed under vacuum to give a tan solid (141 g). Recrystallization from methanol gave 1-cyano-4-phenyl-3,4-dihydronaphthalene (113.6 g, 78%) as a tan solid, m.p. 66°-67° C.

Preparation of 1-Cyano-4-phenyl-1,2,3,4-tetrahydro-2-naphthaleneacetic acid methyl ester To a solution of methanol (150 ml) was added sodium metal (3.58 g, 0.156 m) at ambient temperature under nitrogen. When all of the sodium had been consumed a solution of dimethyl malonate (60 ml, 70 g, 0.53 m) in methanol (30 ml) was added. The solution was stirred at room temperature for 1.5 hr. and cooled to 0° C. A solution of 1-cyano-4-phenyl-3,4-dihydronaphthalene (30.0 g, 0.129 m) in THF (150 ml) and methanol (50 ml) was added dropwise over a period of 2 hr. The solution was allowed to warm to ambient temperature and stirred at that temperature for 60 hr. The reddish reaction mixture was poured into 1N HCl (400 ml) and ethyl acetate-ether (2:1, 300 ml). The phases were separated and the aqueous phase was extracted with ethyl acetate-ether (2:1, 300 ml). The combined organic extracts were washed with saturated NaCl (100 ml), dried over magnesium sulfate and concentrated under vacuum to give a yellow-orange oil (93 g).

The above oil was dissolved in methanol (200 ml) and a solution of potassium hydroxide (70 g, 1.25 m) in methanol (300 ml) and water (300 ml) was added dropwise over a period of 2 hr. The solution was stirred at ambient temperature under nitrogen for 18 hr. The reaction mixture was poured into water (600 ml) and extracted with ether (3×200 ml). The combined ether extracts were extracted with 10% sodium hydroxide (100 ml).

The combined aqueous phases were acidified to pH=1 with concentrated HCl and extracted with ethyl acetate (2×400 ml). The combined ethyl acetate extracts were washed with saturated sodium chloride (100 ml) and dried over magnesium sulfate. Evaporation of solvents gave 66 g of an orange oil.

The above orange oil was dissolved in DMF (150 ml) and heated to 135° C. for 4 hr. The solution was cooled to ambient temperature and poured into water (600 ml). The solution was extracted with ethyl acetate-ethyl ether (1:1, 3×200 ml). The combined organic extracts were washed with water (3×500 ml), saturated sodium chloride (200 ml) and dried over magnesium sulfate. Evaporation of solvents gave 40.62 g of a tan oil.

To a solution of the above oil in methanol (250 ml) was added concentrated sulfuric acid (1 ml) and the solution was stirred at ambient temperature under nitrogen overnight. The solid which had formed was removed by filtration to give 8.36 g (21%) of (±)-(1α,2α,4α)-1-cyano-4-phenyl-1,2,3,4-tetrahydro-2-naphthaleneacetic acid methyl ester. The filtrate was poured into water (500 ml) and 1N NaHCO$_3$ (100 ml) and extracted with ethyl ether (2×300 ml) and ethyl acetate (250 ml). The combined organic extracts were washed with 1N NaHCO$_3$ (100 ml), saturated sodium chloride (100 ml) and dried over magnesium sulfate. Evaporation of solvents gave 26.43 g of a tan oil. The above oil was purified (four injections of approximately 6.5 g) by chromatography on a Prep 500 HPLC on silica gel eluting with ethyl acetate-hexane (1:9). Two major fractions were obtained; the less polar fraction (13.01 g, 33%) was a 3:2 mixture of (±)-(1α,2β,4β)-cyano-4-phenyl-1,2,3,4-tetrahydro-2-naphthaleneacetic acid methyl ester and (±)-(1α,2α,4β)-1-cyano-4-phenyl-1,2,3,4-tetrahydro-2-naphthaleneacetic acid methyl ester. Fractional recrystallization from ethyl ether-hexane followed by recrystallization from methanol and vacuum drying at 60° C. for 48 hr. gave 2.1 g of (±)-(1α,2β,4β)-1-cyano-4-phenyl-1,2,3,4-tetrahydro-2-naphthaleneacetic acid methyl ester, m.p. 103°–105° C., and 0.35 g of (±)-(1α,2α,4β)-1-cyano-4-phenyl-1,2,3,4-tetrahydro-2-naphthaleneacetic acid methyl ester, m.p. 114°–116° C. The more polar fraction (9.61 g, 24%) was a 2:1 mixture of (±)-(1α,2β,4α)-1-cyano-4-phenyl-1,2,3,4-tetrahydro-2-naphthaleneacetic acid methyl ester and (±)-(1α,2α,4α)-1-cyano-4-phenyl-1,2,3,4-tetrahydro-2-naphthaleneacetic acid methyl ester. Crystallization from methanol gave 2.55 g of (±)-(1α,2α,4α)-1-cyano-4-phenyl-1,2,3,4-tetrahydro-2-naphthaleneacetic acid methyl ester, m.p. 120°–121° C. Evaporation of solvent from the filtrate gave 6.02 g of (±)-(1α,2β,4α)-1-cyano-4-phenyl-1,2,3,4-tetrahydro-2-naphthaleneacetic acid methyl ester, as a light yellow oil; 200 MHz NMR (CDCl$_3$) 7.49 (1H, d, J=9 Hz), 7.38–7.08 (6H, m), 7.08–6.93 (3H, m), 4.22 (1H, t, J=6.4 Hz), 4.08 (1H, d, J=8.5 Hz), 3.66 (3H, s), 2.85–2.40 (3H, m), 2.33–1.74 (2H, m).

Anal. Calc. for C$_{20}$H$_{19}$NO$_2$: C, 78.66; H, 6.27, N, 4.59. Found: C, 78.60; H, 6.51; N, 4.27.

Preparation of (±)-(4aα,6α,10bβ)-6-Phenyl-1,4,4a,5,6,10b-hexahydrobenz(h)isoquinolin-3(2H)-one To a solution of (±)-(1α,2β,4α)-1-cyano-4-phenyl-1,2,3,4-tetrahydro-2-naphthaleneacetic acid methyl ester (5.6 g, 0.018 m) in acetic acid (50 ml), methanol (40 ml) and THF (40 ml) in a pressure bottle was added platinum oxide (1.2 g). The mixture was hydrogenated on a Parr apparatus for 24 hr. at a pressure of 40 psi. The precipitate which had formed was dissolved by the addition of THF (100 ml) and the catalyst was removed by filtration. The solution was concentrated under vacuum and the residue was stirred in a two phase mixture of chloroform (200 ml) and 1N sodium carbonate (100 ml). The precipitate which had formed was removed by filtration. The phases were separated and the chloroform phase was dried over magnesium sulfate. Removal of solvent under vacuum gave a white solid which was combined with the solid collected by filtration to give 5.09 g of crude product. Recrystallization from chloroform-methanol gave 3.6 g (71%) of (±)-(4aα,6α,10bβ)-6-phenyl-1,4,4a,5,6,10b-hexahydrobenz(h)isoquinoline-3(2H)-one, m.p. 268°–270° C. (D).

Preparation of (±)-(4aα,6β,10bα)-6-Phenyl-1,4,4a,5,6,10b-hexahydrobenz(h)isoquinolin-3(2H)-one To a solution of (±)-(1α,2α,4α)-1-cyano-4-phenyl-1,2,3,4-tetrahydro-2-naphthaleneacetic acid methyl ester (2.01 g, 0.00658 m) in acetic acid (15 ml) and methanol (15 ml), in a pressure bottle was added platinum oxide (0.22 g). The mixture was hydrogenated on a Parr apparatus at 40 psi. for 24 hr. TLC analysis indicated that the reaction was complete. The precipitate which had formed was dissolved by the addition of THF (50 ml) and the catalyst was removed by filtration. The solution was concentrated under vacuum to give a white solid, which was suspended in a two phase mixture of chloroform (100 ml) and water (100 ml). The mixture was basified to pH=10 by the addition of sodium carbonate. The phases were separated and the aqueous phase was extracted with chloroform (2×75 ml). The combined chloroform extracts were washed with saturated sodium chloride (75 ml) and dried over magnesium sulfate. Removal of solvent gave a white solid (1.82 g). Recrystallization from methanol-ethyl ether followed by vacuum drying at 60° C. for 120 hr. gave 1.65 g (90%) of (±)-(4aα,6β,10bα)-6-phenyl-1,4,4a,5,6,10b-hexahydrobenz(h)isoquinoline-3(2H)-one, m.p. 242°–243° C.

Following essentially the same procedure but substituting (±)-(1α,2α,4β);
(±)-(1α,2β,4β);

-1-cyano-4-phenyl-1,2,3,4-tetrahydro-2-naphthaleneacetic acid methyl ester for (±)-(1α,2α,4α)-1-cyano-4-phenyl-1,2,3,4-tetrahydro-2-naphthaleneacetic acid methyl ester above will result in the formation of (±)-(4aα,6α,10bα);
(±)-(4aα,6β,10bβ);

-6-phenyl-1,4,4a,5,6,10b-hexahydrobenz(h)isoquinolin-3(2H)-one, respectively.

EXAMPLES OF THE PREPARATION OF COMPOUNDS OF FORMULA 1

EXAMPLE 1

Preparation of (±)-(4aα,6α,10bβ)-6-phenyl-1,2,3,4,4a,5,6,10b-octahydrobenz(h)isoquinoline (Z)-2-butenedioate (1:1) salt To a suspension of (±)-(4aα,6α,10bβ)-6-phenyl-1,4,4a,5,6,10b-hexahydrobenz(h)isoquinolin-3(2H)-one (3.5 g, 0.013 m) in THF (80 ml) at 0° C. under nitrogen was added lithium aluminum hydride (0.90 g 0.024 m). The mixture was warmed to room temperature and then refluxed for 5 hr. Thin layer chromatography (TLC) analysis showed the reaction to be complete. The reaction was cooled to 0° C. and water (1 ml), 15% sodium hydroxide (1 ml) and water (3 ml) were carefully added. The mixture was warmed to ambient temperature and the precipitated salt were removed by filtration through celite. The filter cake was washed with chloroform (3×25 ml). The filtrate was concentrated under vacuum to give a white solid (3.4 g).

To a solution of the above amine in methanol (50 ml) was added maleic acid (1.50 g) and the solution was stirred at room temperature for 1 hr. The salt which formed was removed by filtration to give 3.59 g of white solid. Filtration with methanol at reflux and vacuum drying at 65° C. for 120 hr. gave 3.28 g (67%) of (±)-(4aα,6α,10bβ)-6-phenyl-1,2,3,4,4a,5,6,10b-octahydrobenz(h)isoquinoline (Z)-2-butenedioate (1:1) salt, m.p. 196°–197° C.

EXAMPLE 2

Preparation of (±)-(4aα,6β,10bα)-6-phenyl-1,2,3,4,4a,5,6,10b-octahydrobenz(h)isoquinoline (Z)-2-butenedioate (1:1) salt To a suspension of (±)-(4aα,6β,10bα)-6-phenyl-1,4,4a,5,6,10b-hexahydrobenz(h)isoquinolin-3(2H)-one (5.34 g, 0.019 m) in THF (40 ml) at ambient temperature under nitrogen was added dropwise a solution of borane-THF complex (96 ml of 1M solution, 0.096 m). The solution was heated to reflux overnight and then cooled to 0° C. To the solution was added 15% HCl (100 ml) dropwise. The reaction mixture was heated to reflux for 1 hr. and then cooled to ambient temperature. The reaction was basified to pH=11 with 50% NaOH and extracted with chloroform (2×100 ml). The combined chloroform extracts were washed with water (75 ml), saturated sodium chloride (75 ml) and dried over magnesium sulfate. The solution was concentrated under vacuum to give a white solid (10.2 g).

The above solid was added to a solution of methanol (50 ml), water (50 ml) and concentrated hydrochloric acid (50 ml). The solution was heated to reflux for 1 hr. and then cooled to ambient temperature. The reaction was poured into water (200 ml) and basified with 50% NaOH to pH=11. The aqueous solution was extracted with chloroform (3×100 ml). The chloroform extracts were washed with water (75 ml) and dried over magnesium sulfate. Evaporation of the solvents gave 6.01 g of a yellow oil which crystallized on standing.

The above solid was dissolved in acetone (50 ml). To this solution was added maleic acid (2.20 g, 0.019 m). The reaction was stirred at ambient temperature for 0.5 hr. and the precipitated salt was isolated by filtration. Filtration of this solid with acetone at reflux and vacuum drying at 60° C. for 120 hr. gave 3.39 g (47%) of (±)-(4aα,6β,10bα)-6-phenyl-1,2,3,4,4a,5,6,10b-octahydrobenz(h)isoquinoline (Z)-2-butenedioate (1:1) salt, m.p. 178°–179° C.

Following essentially the same procedure but substituting
(±)-(4aα,6α,10bα);
(±)-(4aα,6β,10bβ);
-6-phenyl-1,4,4a,5,6,10b-hexahydrobenz(h)isoquinolin-3(2H)-one for (±)-(4aα,6β,10bα)-6-phenyl-1,4,4a,5,6,10b-hexahydrobenz(h)isoquinolin-3(2H)-one above will result in the formation of
(±)-(4aα,6α,10bα);
(±)-(4aα,6β,10bβ);
-6-phenyl-1,2,3,4,4a,5,6,10b-octahydrobenz(h)isoquinoline (Z)-2-butenedioate (1:1) salt.

EXAMPLE 3

Preparation of (±)-(4aα,6α,10bβ)-2-Methyl-6-phenyl-1,2,3,4,4a,5,6,10b-octahydrobenz(h)isoquinoline (Z)-2-butenedioate (1:1) salt To a solution of (±)-(4aα,6α,10bβ)-6-phenyl-1,2,3,4,4a,5,6,10b-octahydrobenz(h)isoquinoline (5.40 g, 0.021 m) in 88% formic acid (12.5 ml) was added 37% aqueous formaldehyde (20 ml) and the solution was heated to reflux under nitrogen for 1 hr. TLC analysis indicated that the reaction was complete. The solution was cooled to ambient temperature and poured onto a mixture of ice (~50 g), water (100 ml) and chloroform (75 ml). The mixture was basified to pH=11 with concentrated ammonium hydroxide. The phases were separated and the aqueous phase was extracted with chloroform (2×100 ml). The combined chloroform extracts were washed with water (75 ml). The chloroform solution was dried over magnesium sulfate and the solvent was removed under vacuum to give a yellow solid (5.69 g, 100%).

The above solid was dissolved in dichloromethane (20 ml). To this solution was added a solution of maleic acid (2.51 g, 0.0216 m) in acetone (15 ml). After stirring the solution at ambient temperature for a few minutes a precipitate formed. Ether (80 ml) was added and the precipitate was isolated by filtration. The solid was triturated with ethyl acetate-acetone (1:1, 50 ml) at reflux. The solution was cooled to ambient temperature and the solid was isolated by filtration and vacuum dried at 60° C. for 72 hr. to give 3.91 g (47%) of (±)-(4aα,6α,10bβ)-2-methyl-6-phenyl-1,2,3,4,4a,5,6,10b-octahydrobenz(h)isoquinoline (z)-2-butendioate (1:1) salt, m.p. 192°–194° C. (D).

EXAMPLE 4

Preparation of (±)-(4aα,6β,10bα)-2-Methyl-6-phenyl-1,2,3,4,4a,5,6,10b-octahydrobenz(h)isoquinoline (Z)-2-butenedioate (1:1) salt To a solution of (±)-(4aα,6β,10bα)-6-phenyl-1,2,3,4,4a,5,6,10b-octahydrobenz(h)isoquinoline (4.50 g, 0.017 m) in 88% formic acid (15 ml) was added 37% aqueous formaldehyde (20 ml) and the solution was heated to reflux under nitrogen for 1 hr. The reaction was cooled to ambient temperature and poured onto ice (50 g) and water (50 ml). The solution was basified with concentrated ammonium hydroxide and extracted with chloroform (3×100 ml). The combined chloroform extracts were washed with saturated sodium chloride (75 ml) and dried over magnesium sulfate. Evaporation of the solvents gave 4.54 g of a yellow oil.

The above oil was dissolved in dichloromethane (25 ml). To this solution was added a slurry of maleic acid (1.90 g, 0.016 m) in dichloromethane (15 ml). The resulting solution was stirred at ambient temperature for 0.5 hr. The solution was poured into ethyl ether (150 ml) and the resulting precipitate was isolated by filtration. The above solid was suspended in acetone (50 ml) and warmed to reflux. The solution was cooled to ambient temperature and the salt was isolated by filtration. Vacuum drying at 60° C. for 120 hr. gave 4.36 g (65%) of (±)-(4aα,6β,10bα)-2-methyl-6-phenyl-1,2,3,4,4a,5,6,10b-octahydrobenz(h)isoquinoline (z)-2-butenedioate (1:1) salt, m.p. 217°–219° C. (D).

Following essentially the same procedure but substituting
(±)-(4aα,6α,10bα);
(±)-(4aα,6β,10bβ);
-6-phenyl-1,2,3,4,4a, 5,6,10b-octahydrobenz(h)isoquinoline for (±)-(4aα,6β,10bα)-6-phenyl-1,2,3,4,4a,5,6,10b-octahydrobenz(h)isoquinoline for will result in the formation of
(±)-(4aα,6α,10bα);
(±)-(4aα,6β,10bβ);
-2-methyl-6-phenyl-1,2,3,4,4a,5,6,10b-octahydrobenz(h)isoquinoline (Z)-2-butenedioate (1:1) salt, respectively.

Application of the methodology described above will provide all the compounds of the invention including, for example, the following 1,2,3,4,4a,5,6,10b-octahydrobenz(h)isoquinolines (including all of their stereoisomeric forms):

6-(4-bromophenyl)-1,2,3,4,4a,5,6,10b-octahydrobenz(h)isoquinoline (Z)-2-butenedioate; 6-[4-(trifluoromethyl)phenyl]-1,2,3,4,4a,5,6,10b-octahydrobenz(h)isoquinoline (Z)-2-butenedioate; 6-(2,4-dichlorophenyl)-1,2,3,4,4a,5,6,10b-octahydrobenz(h)isoquinoline (Z)-2-butenedioate; 6-(3-methoxy-4-fluorophenyl)-1,2,3,4,4a,5,6,10b-octahydrobenz(h)isoquinoline (Z)-2-butenedioate; 6-(4-methoxyphenyl)-1,2,3,4,4a,5,6,10b-octahydrobenz(h)isoquinoline (Z)-2-butenedioate; 6-(4-n-butoxyphenyl)-1,2,3,4,4a,5,6,10b-octahydrobenz(h)isoquinoline (Z)-2-butenedioate; 6-(4-phenoxyphenyl)-1,2,3,4,4a,5,6,10b-octahydrobenz(h)isoquinoline (Z)-2-butenedioate; 6-(2-chlorophenyl)-1,2,3,4,4a,5,6,10b-octahydrobenz(h)isoquinoline (Z)-2-butenedioate; 6-(4-methylphenyl)-1,2,3,4,4a,5,6,10b-octahydrobenz(h)isoquinoline (Z)-2-butenedioate; 9-methoxy-6-phenyl-1,2,3,4,4a,5,6,10b-octahydrobenz(h)isoquinoline (Z)-2-butenedioate; 9-methoxy-6-(4-methoxyphenyl)-1,2,3,4,4a,5,6,10b-octahydrobenz(h)isoquinoline (Z)-2-butenedioate; 9-methyl-6-(2,4,6-trimethylphenyl)-1,2,3,4,4a,5,6,10b-octahydrobenz(h)isoquinoline (Z)-2-butenedioate; 9-chloro-6-(4-chlorophenyl)-1,2,3,4,4a,5,6,10b-octahydrobenz(h)isoquinoline (Z)-2-butenedioate; 2-methyl-6-(4-bromophenyl)-1,2,3,4,4a,5,6,10b-octahydrobenz(h)isoquinoline (Z)-2-butenedioate; 2-methyl-6-(4-methoxyphenyl)-1,2,3,4,4a,5,6,10b-octahydrobenz(h)isoquinoline (Z)-2-butenedioate; 2-methyl-9-methoxy-6-phenyl-1,2,3,4,4a,5,6,10b-octahydrobenz(h)isoquinoline (Z)-2-butenedioate; 2-heptyl-6-[4-(trifluoromethyl)phenyl]-1,2,3,4,4a,5,6,10b-octahydrobenz(h)isoquinoline (Z)-2-butenedioate; 2-heptyl-10-chloro-7-methoxy-6-phenyl-1,2,3,4,4a,5,6,10b-octahydrobenz(h)isoquinoline (Z)-2-butenedioate; 2-heptyl-6-(2-chlorophenyl)-1,2,3,4,4a,5,6,10b-octahydrobenz(h)isoquinoline (Z)-2-butenedioate; 2-heptyl-6-(4-methylphenyl)-1,2,3,4,4a,5,6,10b-octahydrobenz(h)isoquinoline (Z)-2-butenedioate; 2-cyclopropylmethyl-6-(3-methoxyphenyl)-1,2,3,4,4a,5,6,10b-octahydrobenz(h)isoquinoline (Z)-2-butenedioate; 2-cyclopropylmethyl-6-(2-fluorophenyl)-1,2,3,4,4a,5,6,10b-octahydrobenz(h)isoquinoline (Z)-2-butenedioate; 2-cyclopropylmethyl-8,9-dimethoxy-6-(3,4-dimethoxyphenyl)-1,2,3,4,4a,5,6,10b-octahydrobenz(h)isoquinoline (Z)-2-butenedioate; 6-(4-hydroxyphenyl)-1,2,3,4,4a,5,6,10b-octahydrobenz(h)isoquinoline (Z)-2-butenedioate; and 9-hydroxy-6-(4-methylphenyl)-1,2,3,4,4a,5,6,10b-octahydrobenz(h)isoquinoline (Z)-2-butenedioate.

What is claimed is:

1. A compound of the formula

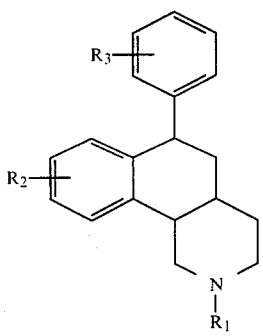

wherein $R_1$ is hydrogen, $C_1$–$C_7$ alkyl, or $C_4$–$C_8$ cycloalkylmethyl;

$R_2$ is hydrogen or a single or multiple substitution of hydroxyl, halogen, $C_1$–$C_7$ alkoxy, or $C_1$–$C_7$ alkyl; and $R_3$ is hydrogen or a single or multiple substitution of hydroxyl, halogen, $C_1$–$C_7$ alkoxy, phenoxy, $C_1$–$C_7$ alkyl, or trifluoromethyl; all stereoisomeric forms and mixtures thereof, and pharmaceutically acceptable addition salts thereof.

2. A compound of the formula in claim 1, wherein $R_1$ is defined as in claim 1; $R_2$ is hydrogen or a single or double substitution of hydroxyl, halogen, $C_1$–$C_7$ alkoxy, or $C_1$–$C_7$ alkyl; and $R_3$ is hydrogen or a single or double substitution of, hydroxyl, halogen, $C_1$–$C_7$ alkoxy, phenoxy, $C_1$–$C_7$ alkyl or trifluoromethyl; all stereoisomeric forms and mixtures thereof, and pharmaceutically acceptable salts thereof.

3. The racemate as defined in claim 1 which is ($\pm$)-(4a$\alpha$,6$\alpha$,10b$\beta$)-6-phenyl-1,2,3,4,4a,5,6,10b-octahydrobenz(h)isoquinoline (Z)-2-butenedioate and pharmaceutically acceptable salts thereof.

4. The racemate as defined in claim 1 which is ($\pm$)-(4a$\alpha$,6$\beta$,10b$\alpha$)-6-phenyl-1,2,3,4,4a,5,6,10b-octahydrobenz(h)-isoquinoline (Z)-2-butenedioate and pharmaceutically acceptable salts thereof.

5. The racemate as defined in claim 1 which is ($\pm$)-(4a$\alpha$,6$\alpha$,10b$\beta$)-2-methyl-6-phenyl-1,2,3,4,4a,5,6,10b-octahydrobenz(h)isoquinoline (Z)-2-butenedioate and pharmaceutically acceptable salts thereof.

6. The racemate as defined in claim 1 which is ($\pm$)-(4a$\alpha$,6$\beta$,10b$\alpha$)-2-methyl-6-phenyl-1,2,3,4,4a,5,6,10b-octahydrobenz(h)isoquinoline (Z)-2-butenedioate and pharmaceutically acceptable salts thereof.

7. The method of treating depression comprising the administration of an effective amount of a compound of claim 1 to a human in need of such treatment.

* * * * *